US012432122B2

(12) United States Patent
Rangarajan et al.

(10) Patent No.: US 12,432,122 B2
(45) Date of Patent: Sep. 30, 2025

(54) ARTIFICIAL INTELLIGENCE INTEGRATOR

(71) Applicant: International Business Machines Corporation, Armonk, NY (US)

(72) Inventors: Arvind Rangarajan, Chennai (IN); Pradeep Raj Jayarathanasamy, Chennai (IN); Srithar Rajan Thangaraj, Chennai (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 226 days.

(21) Appl. No.: 18/456,766

(22) Filed: Aug. 28, 2023

(65) Prior Publication Data

US 2025/0077311 A1 Mar. 6, 2025

(51) Int. Cl.
| | |
|---|---|
| *G06F 8/30* | (2018.01) |
| *G06F 8/35* | (2018.01) |
| *G06F 9/54* | (2006.01) |
| *G06N 20/00* | (2019.01) |
| *H04L 41/16* | (2022.01) |
| *G06Q 10/0637* | (2023.01) |

(Continued)

(52) U.S. Cl.
CPC ............... *H04L 41/16* (2013.01); *G06F 8/35* (2013.01); *G06F 9/541* (2013.01); *G06N 20/00* (2019.01); *G06Q 10/06375* (2013.01); *G06Q 20/02* (2013.01); *G16B 50/20* (2019.02); *H04L 45/306* (2013.01); *H04W 24/08* (2013.01)

(58) Field of Classification Search
CPC ....... G06Q 20/02; H04W 24/08; H04L 41/16; G06F 9/541
See application file for complete search history.

(56) References Cited

U.S. PATENT DOCUMENTS

| | | |
|---|---|---|
| 10,944,654 B2 | 3/2021 | Rimar et al. |
| 2004/0154000 A1 | 8/2004 | Kasravi et al. |

(Continued)

OTHER PUBLICATIONS

Sah, A., Rawat, S., & Pundir, S. (Sep. 1, 2012). Design, implementation and integration of heterogeneous applications. International Journal of Computer Applications, 54(5).

(Continued)

*Primary Examiner* — Tuan A Vu
(74) *Attorney, Agent, or Firm* — Tutunjian & Bitetto, P.C.; Andre L. Adkins

(57) ABSTRACT

A method for integrating heterogeneous systems is presented including initiating a conversation between a consumer system having a first artificial intelligence (AI) integrator and a producer system having a second AI integrator, training the first and second AI integrators to enable the conversation between the consumer system and the producer system, upon a data request from a client, enabling the consumer system to receive an application programming interface specification (API Spec) and locate the producer system that provides service in conformance with the API Spec, determining missing data needed to conform to the API Spec to build source code, if the producer system determines that it can support the data request, triggering the producer system to generate a contract, and after consensus is provided, in a deployment phase, generating by the producer system the source code to provide information pertaining to the data request.

20 Claims, 7 Drawing Sheets

(51) Int. Cl.
*G06Q 20/02* (2012.01)
*G16B 50/20* (2019.01)
*H04L 45/302* (2022.01)
*H04W 24/08* (2009.01)

(56) References Cited

U.S. PATENT DOCUMENTS

| | | | |
|---|---|---|---|
| 2006/0005204 A1 | 1/2006 | Siegel et al. | |
| 2018/0068132 A1 | 3/2018 | Zubair et al. | |
| 2021/0192412 A1* | 6/2021 | Krishnaswamy | ............................ G06Q 10/06375 |
| 2022/0129257 A1 | 4/2022 | Touati et al. | |
| 2022/0180319 A1* | 6/2022 | Saxena | .................. G16B 50/20 |
| 2022/0253306 A1 | 8/2022 | Ryan et al. | |
| 2022/0366515 A1* | 11/2022 | Behrends | ............... G06Q 20/02 |
| 2023/0246954 A1* | 8/2023 | Palumbo | ............... H04L 45/306 709/238 |
| 2024/0414067 A1* | 12/2024 | Yao | ........................ H04L 41/16 |
| 2025/0071577 A1* | 2/2025 | Foroughi | .............. H04W 24/08 |

OTHER PUBLICATIONS

El-Sheimy, N., Chiang, K. W., & Noureldin, A. (Oct. 18, 2006). The utilization of artificial neural networks for multisensor system integration in navigation and positioning instruments. IEEE Transactions on instrumentation and measurement, 55(5), 1606-1615.

Authors et al.: Disclosed Without Attribution, "Cognitive Integration Service", IP.com No. IPCOM000252536D, Jan. 22, 2018, 05 pages.

Jensen Anders. "Power Automate Breaking News: You Describe It—AI Builds It", retrieved from web https://www.youtube.com/watch?v=U5ppA3J9qM4&t=77s, Oct. 15, 2022, 3 pages.

Talamadupula et al., "Goal-oriented flow assist_supporting low code data flow automation with natural language" IBM Research, Oct. 3, 2022, 07 pages.

* cited by examiner

ARTIFICIAL INTELLIGENCE INTEGRATOR

BACKGROUND

The present invention relates generally to software integration, and more specifically, to implementing an artificial intelligence (AI) integrator to perform integration between heterogeneous systems.

Software integration remains an issue for companies. Complex architectures and garage methodologies have evolved to solve complex business problems, but no development process has been smooth. Integrating heterogenous systems from across different vendors, with different formats, protocols, and languages grows in complexity and is increasingly time consuming. The workaround for these issues often narrows down to one common category, that is, human-human interaction. It often takes several weeks to months time to discover data requirements, the source systems that provide this data, mechanisms to authenticate, etc. The effort needed to perform the discovery, data mapping, and maintaining client specific versions must be repeated time and time again for every client change and every new client. These tasks are complex and time consuming because there are multiple teams and multiple interactions involved.

SUMMARY

In accordance with an embodiment, a method for integrating heterogeneous systems is provided. The method includes initiating a conversation between a consumer system having a first artificial intelligence (AI) integrator and a producer system having a second AI integrator, training the first and second AI integrators to enable the conversation between the consumer system and the producer system, upon a data request from a client, enabling the consumer system to receive an application programming interface specification (API Spec) and locate the producer system that provides service in conformance with the API Spec, determining missing data needed to conform to the API Spec to build source code, if the producer system determines that it can support the data request, triggering the producer system to generate a contract, and after consensus is provided, in a deployment phase, generating by the producer system the source code to provide information pertaining to the data request.

In accordance with another embodiment, a computer program product is provided for integrating heterogeneous systems, the computer program product comprising a computer readable storage medium having program instructions embodied therewith. The program instructions are executable by a computer to cause the computer to initiate a conversation between a consumer system having a first artificial intelligence (AI) integrator and a producer system having a second AI integrator, train the first and second AI integrators to enable the conversation between the consumer system and the producer system, upon a data request from a client, enable the consumer system to receive an application programming interface specification (API Spec) and locate the producer system that provides service in conformance with the API Spec, determine missing data needed to conform to the API Spec to build source code, if the producer system determines that it can support the data request, trigger the producer system to generate a contract, and after consensus is provided, in a deployment phase, generate by the producer system the source code to provide information pertaining to the data request.

In accordance with yet another embodiment, a system for integrating heterogeneous systems is provided. The system includes a memory and one or more processors in communication with the memory configured to initiate a conversation between a consumer system having a first artificial intelligence (AI) integrator and a producer system having a second AI integrator, train the first and second AI integrators to enable the conversation between the consumer system and the producer system, upon a data request from a client, enable the consumer system to receive an application programming interface specification (API Spec) and locate the producer system that provides service in conformance with the API Spec, determine missing data needed to conform to the API Spec to build source code, if the producer system determines that it can support the data request, trigger the producer system to generate a contract, and after consensus is provided, in a deployment phase, generate by the producer system the source code to provide information pertaining to the data request.

It should be noted that the exemplary embodiments are described with reference to different subject matters. In particular, some embodiments are described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be described within this document.

These and other features and advantages will become apparent from the following detailed description of illustrative embodiments thereof, which is to be read in connection with the accompanying drawings.

BRIEF DESCRIPTION OF THE DRAWINGS

The invention will provide details in the following description of preferred embodiments with reference to the following figures wherein.

Throughout the drawings, same or similar reference numerals represent the same or similar elements.

DETAILED DESCRIPTION

Embodiments in accordance with the present invention provide methods and systems for implementing a conversation-based artificial intelligence (AI) integrator solution which facilitates replacing the need for human interaction and performs integration between heterogenous systems. The AI integrator (referred to as AII) resides on different layers in the integration system. AII learns the system it represents and converses with its counterpart to integrate with the system that the counterpart represents. The process to "learn" is standardized and there is no restriction on the type of system it interacts with, which could be another AI integrator as well. Through a series of "conversations," where one is a requestor and the other a receiver, two AI integrators provide a mapping of the data requested and the data available, and the best pattern to realize the solution. With a final human approval interaction, the realized pattern and mapping are generated as code and deployed.

It is to be understood that the present invention will be described in terms of a given illustrative architecture; however, other architectures, structures, substrate materials and process features and steps/blocks can be varied within the scope of the present invention. It should be noted that certain features cannot be shown in all figures for the sake of clarity. This is not intended to be interpreted as a limitation of any particular embodiment, or illustration, or scope of the claims.

Figure 1:
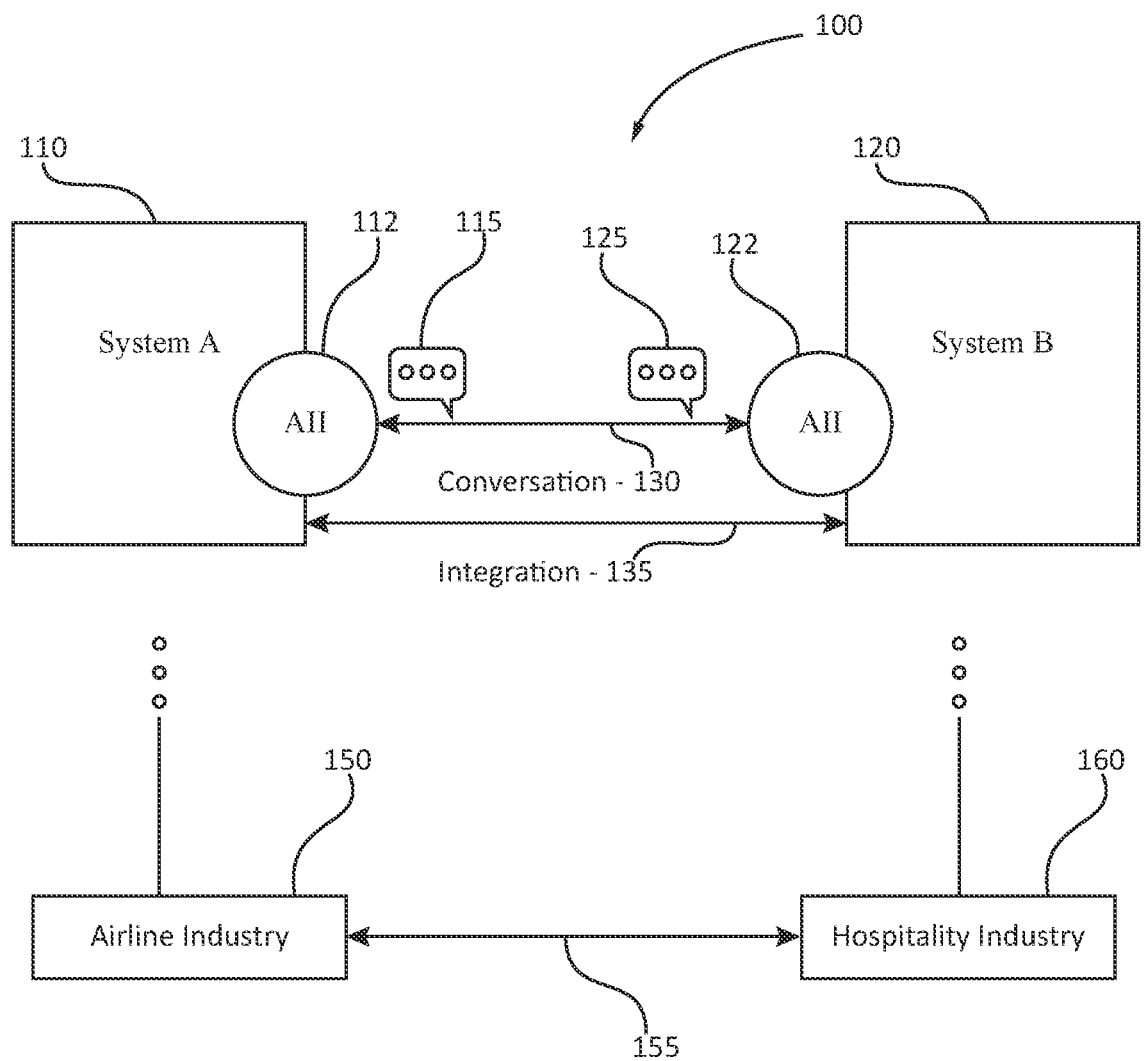
FIG. 1 is a block/flow diagram of an exemplary conversation-based artificial intelligence (AI) integrator configuration, in accordance with an embodiment of the present invention.

FIG. 1 is a block/flow diagram of an exemplary conversation-based artificial intelligence (AI) integrator configuration, in accordance with an embodiment of the present invention.

The exemplary embodiments present a conversation-based AI integrator solution which facilitates replacing the need for human interaction and performs integration 135 between heterogenous systems. The AI integrator (referred to as AII) resides on different layers in the integration system. The AII learns the system it represents and converses with its counterpart to integrate with the system that the counterpart represents. The process to "learn" is standardized and there is no restriction on the type of system it interacts with, which could be another AI integrator as well. Through a series of "conversations," where one is a requestor 115 and the other a receiver 125, the two AI integrators 112, 122 provide a mapping of the data requested and the data available, and the best pattern to realize the solution. With a final human approval interaction, the realized pattern and mapping are generated as code and deployed.

For example, FIG. 1 depicts a conversation-based artificial intelligence (AI) integrator configuration 100 where a System A (110) communicates with a System B (120). The System A (110) includes an AII 112 for conversing with AII 122 of the System B (120). The conversations 130 can be achieved by a requestor 115 and a receiver 125. Thus, dynamic integration of heterogeneous systems with AI interfaces involving iterative cognitive interactions in a polyglot environment can be achieved.

Practical applications can include a scenario where the airline industry 150 expands services with hospitality data from the hospitality industry 160. Thus, conversations 155 are had between the airline industry 150 and the hospitality industry 160. The software used by the airline industry 150 can have a different format, different protocols, and different languages compared to the software used by the hospitality industry 160. However, the AII 112, 122 of the exemplary embodiments of the present invention enable communication between the software of the airline industry 150 and the hospitality industry 160. The AII 112, 122 provide for a mapping of the data requested and the data available pertaining to the software of the airline industry 150 and the hospitality industry 160.

Other practical applications include organizations exposing analytics data for a cost for multiple vendors, integrating data with a new product on the market, an Indian e-commerce system retrieving inventory from a Japanese vendor system, mobile applications integrating with multiple System of Records (SoRs), and retrieving files from a file transfer protocol (FTP) server.

Figure 2:
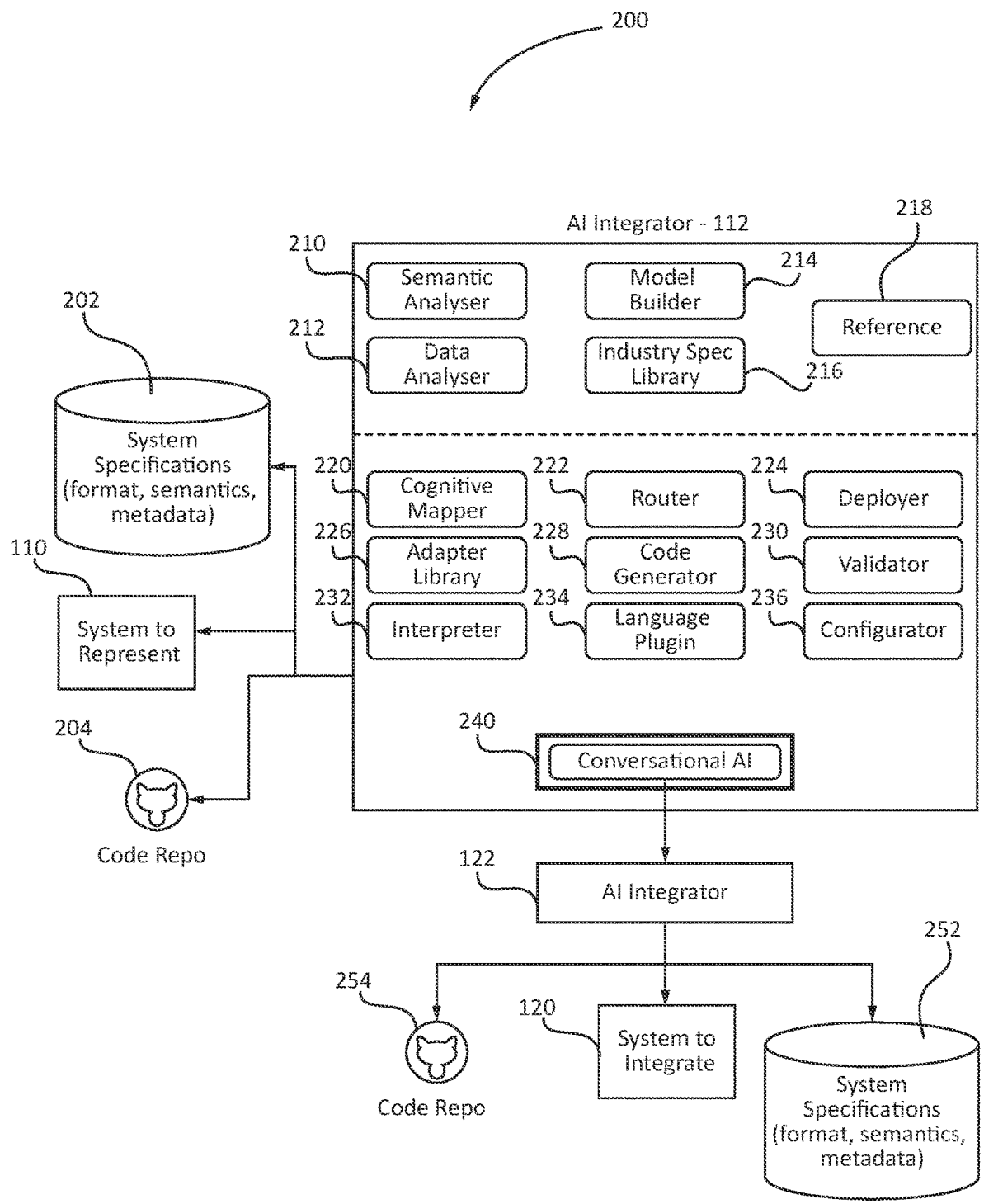
FIG. 2 is a block/flow diagram of exemplary components of the AI integrator, in accordance with an embodiment of the present invention.

FIG. 2 is a block/flow diagram 200 of exemplary components of the AI integrator, in accordance with an embodiment of the present invention.

The system to represent, e.g., the System A (110) includes system specifications 202 and a code repository 204. The code repository 204 is a storage location for code and other software development assets, such as documentation, tests, and scripts. The code repository 204 can be used to manage and organize a software project's codebase and collaborate with other project developers. The System A (110) includes an AI integrator 112.

The AI integrator 112 includes a semantic analyzer 210, a data analyzer 212, a model builder 214, an industry specification library 216, and a reference 218. The AI integrator 112 further includes a cognitive mapper 220, a router 222, a deployer 224, an adapter library 226, a code generator 228, a validator 230, an interpreter 232, a language plugin 234, and a configurator 236. A conversational AI component 240 of the AI integrator 112 communicates with the AI integrator 122 of the system to integrate, that is, the System B (120). The System B (120) includes system specifications 252 and a code repository 254.

Regarding the AII training for conversation, the following steps are performed:

Performing Natural Language Processing (NLP) for understanding or determining intents in a request/response from the heterogeneous systems.

Creating an application programming interface (API) spec that has the delta data needed which can be secured from the producer AI integrator. The API spec or specification details the functional and expected behavior of the API, as well as the fundamental design philosophy and supported data types. The API specification includes both documentation and API definitions to create a contract that people and software can read. Stated differently, the API specification provides a comprehensive understanding of how an API behaves and links with other APIs. The API specification also explains how the API functions and the results to expect when using the API.

In case of a producer AI integrator, understanding the spec requirement and responding with consent to provide the data is needed.

Understanding the API spec and an authentication mechanism of the target system are further provided.

Next, establishing consensus on the spec is needed.

Subsequently, securing credentials, sending a request, and validating the API response compliance with the spec are performed.

Finally, negotiating pricing and establishing consensus on the pricing takes place.

Regarding the AII training for API spec understanding, the following steps are performed:

Breaking the entities, attributes, and relationships.

Comparing with the AII's own specification with the help of similarity algorithms and natural language processing (NLP).

Finding deviation, that is, new elements, naming differences, altered relationships, etc.

Regarding alignment of the API spec, from the deviations identified, the exemplary methods check for alternate AII sources from where the new elements can be selected. The sources can be selected either from a static configuration or from a marketplace dynamically choosing the appropriate one based on training.

Regarding AI conversations with other AII systems, the exemplary methods initiate conversations with other source AII systems to check for design mapping and map from different AII source systems to create the client's API request in compliance to its API spec.

Regarding code generation and deployment, the exemplary methods generate code using AI-based systems like GPT-3, OpenAI Codex, and deploy the code on configured run time.

Figure 3:
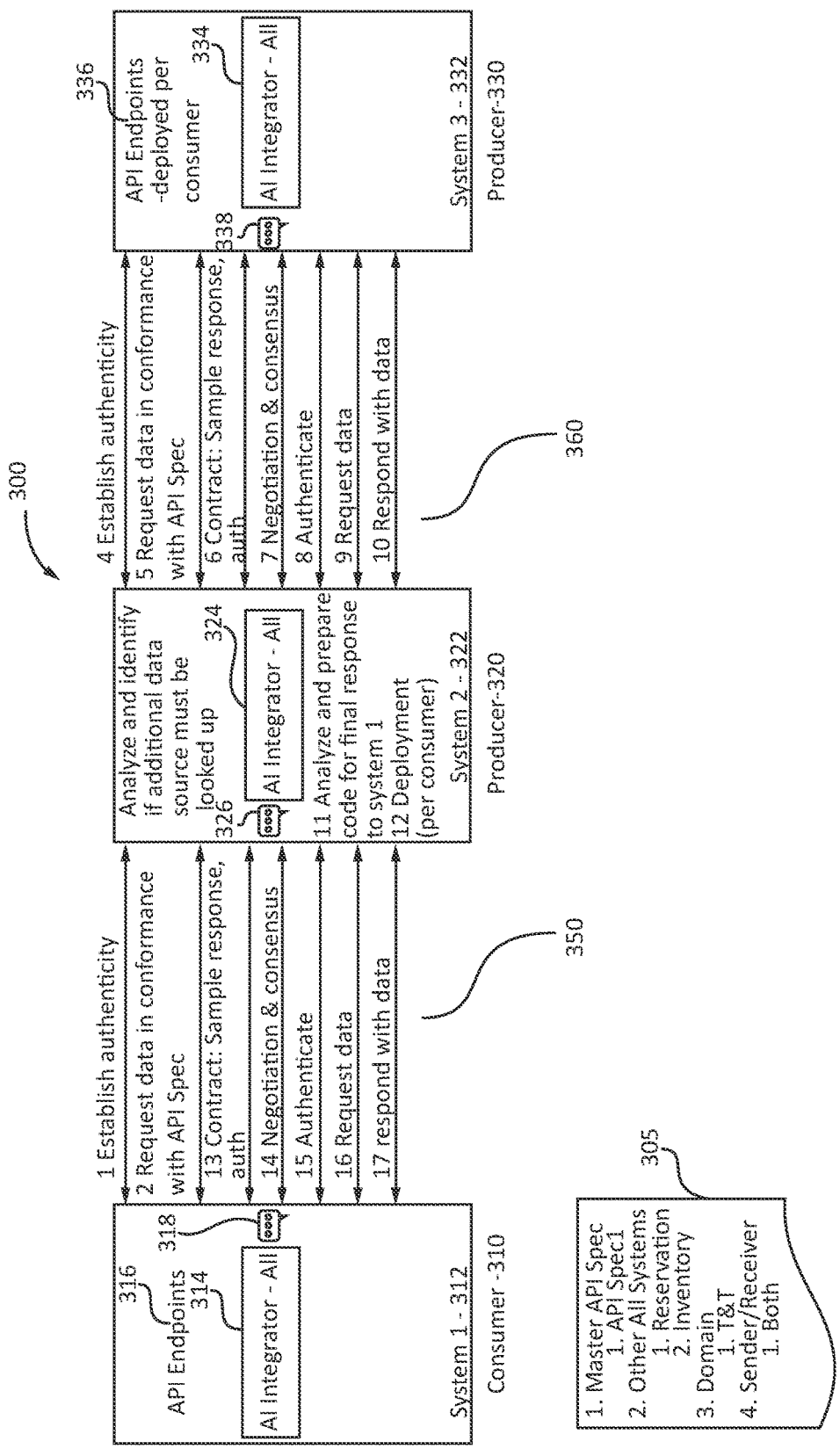
FIG. 3 is a block/flow diagram of exemplary AI integrator communications, in accordance with an embodiment of the present invention.

FIG. 3 is a block/flow diagram of exemplary AI integrator communications 300, in accordance with an embodiment of the present invention.

For the consumer 310, the first system 312 includes an AI integrator 314 with a requester 318 having API endpoints 316. The consumer 310 communicates with a producer 320. The second system 322 of the producer 320 includes an AI integrator 324 and a provider 326 to analyze and identify if additional data sources must be looked up. The communications 350 can include establishing authenticity and requesting data in conformance with the API spec.

If the second system 322 assesses and determines that all of the data in the API spec could not be fulfilled by itself, further communications with a third system 332 of a producer 330 is employed. The communications 360 can include establishing authenticity and requesting data in conformance with the API spec. The third system 332 includes an AI integrator 334, as well as a provider 338 where API endpoints 336 are deployed per customer.

After establishing authenticity and requesting data in conformance with the API spec, the third system 332 sends further communications to the second system 322. The communications 360 further include sample responses, negotiation and consensus, authentication, data requests, and respond with the data.

The second system 322 sends the sample responses, negotiation and consensus, authentication, data requests, and respond with the data to the first system 312.

The AII system is configured initially with a Summary list 305 to provide additional context such as its operating environment, supported specifications, domain, etc.

Therefore, the AII system is trained to converse with other AII systems to understand its role viz consumer or provider, understand the input/output needs, understand the format, business context and perform mapping between the system context summary (e.g., domain) with the input/output.

The AII is trained to understand where the AII fits in the overall architecture. That is, if the AII is a client component or server component and within the server side, if the AII is a network component or an infrastructure component, etc. Based on the position, conversation for integration can be adapted.

The AII also is trained to understand the specification of different software such as SAP, Salesforce, etc. in the context of integration.

Next, the client requests data from the AII.

The AII, from a consumer system, receives the API spec and starts looking for a producer system that can provide a service in conformance with the API spec.

The consumer and producer systems converse to understand the missing data needed to conform to the spec and build the required source code by leveraging AI.

The producer system understands the spec based on its training of understanding a spec in context with business. The producer system determines whether it could understand and map all the requested data. If the producer system finds that there are data that are missing, the producer system can reach out to other configured AII systems to get the missing data. If the producer system determines that it can support the data request, the producer system creates or generates a contract that has the following, e.g., a sample response that satisfies the spec, an authentication mechanism to be used to consume the service, data format, and pricing information.

In an evaluation phase, the consumer system evaluates the response, interprets the authentication mechanism, and, if in agreement, provides consensus. The evaluation includes evaluation of data sufficiency, that is, not all data might be available from the producer system, data format compatibility, and pricing (in case of external systems) assessment for determining whether it is within a threshold.

In a deployment phase, once consensus is in place, the deployment phase kicks in. The producer system generates the code that can pull data from its own system and data from the third system 332 (FIG. 3) and merge such data to comply with the specification of the first system 312.

The consumer system now can start using the producer AII system to get the data. The consumer system secures credentials and establishes authentication and requests the API service to the producer system. The producer system now will start providing the service.

Figure 4:
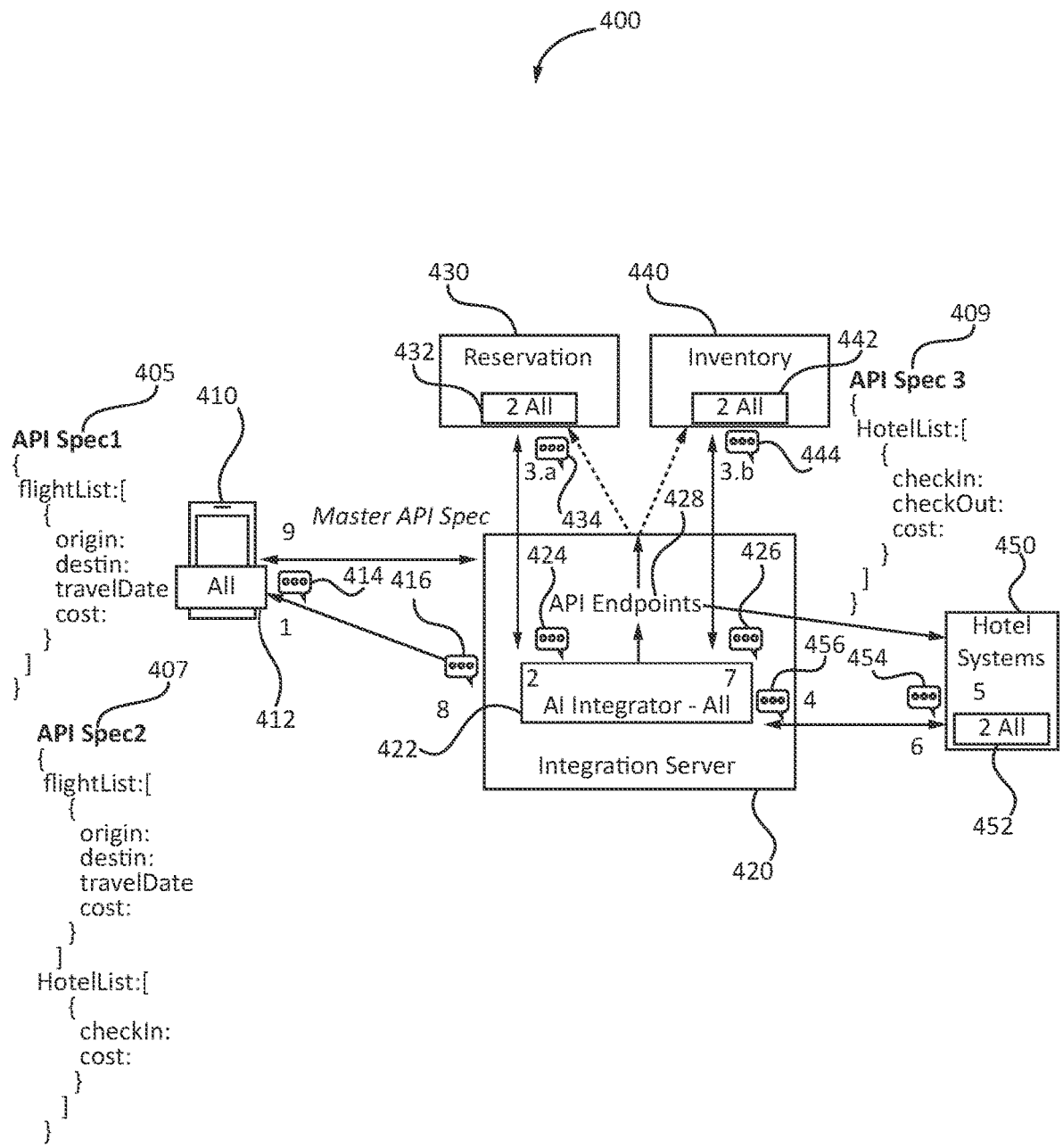
FIG. 4 is a block/flow diagram of an exemplary practical application for implementing the AI integrator, in accordance with an embodiment of the present invention.

Therefore, according to FIGS. 3 and 4, the exemplary system and methods provide for a cognitive conversational system capable of acting as both requestor and consumer, using conversational AI to integrate, intelligent mapping of two software specifications, intelligent mapping of two software specifications in different languages, understanding semantics of a complex software system, and understanding context of software integration.

FIG. 4 is a block/flow diagram of an exemplary practical application for implementing the AI integrator, in accordance with an embodiment of the present invention.

The practical application 400 demonstrates how the AII solution supports an incremental request for data between API spec 1 (405) and API spec 2 (407). In particular:

The AII 412 from a client 410 initiates an AI conversation with another AII 422 in the backend with provider 416. The AII 412 requests for a model/API spec different from the one it has been using to communicate with the backend. For example, hotel availability is the additional data requested by requestor 414. The request has a new API spec, that is, API spec 2 (407) that the client 410 wants.

The AII 422 of the integration server 420 inspects the new API spec (step 2), understands that it is a travel and transportation domain, and identifies the new data requests, in this case, a hotel list. The AII 422 then creates an API spec 3 (409) which helps satisfy the missing fields to service the API spec 2 (407). The AII 422 first searches if this data can be picked up from any of internal AII systems.

Now all internal AII systems follow step 2 and respond back to the initiating AII 412. It is assumed that the internal AII systems do not have the requested data. The systems can include a reservation system 430 with a reservation AII interface 432 and an inventory system 440 with an inventory interface 442. The reservation AII interface 432 can have a provider 434 and the inventory interface 442 can have a provider 444 to communicate with the requestor/provider 424/426 of the AII 422 with API endpoints 428. The systems can request the data from the reservation system 430 and the inventory system 440 (when the data is missing or deficient).

Now the initiating AII 412 looks up to its metadata or AII registry to find the target system it can reach out for the hotel list and initiates the conversation with other external AII systems. The initiating AII 412 starts with requesting support for API spec 3 (409).

The hotel system 450 which has an interface for AII 452 receives the request by provider 454 from requestor 456 and follows step 2 to determine if it can satisfy the API request. It is assumed that it can satisfy the request.

The hotel system's AII 452 now acts as sender AII, and it confirms that it can satisfy the API spec 3 (409). Further, the AII 452 provides the credentials needed to request the data (say as REST).

The initiating AII 412 now creates/updates APIs that can now intelligently merge API spec 1 (405) that it already supports along with API spec 3 (409), to create the new API spec 2 (407) that was initially requested by the client 410. The new APIs are deployed and ready to be consumed by the client 410.

The backend AII now conveys that the API is deployed, and API calls can be placed.

The client 410 starts making requests with new API spec 2 (407). Once tested and validated, the same build can be moved to production with appropriate endpoint configurations. The numbering allows the reader to follow the flow of how the AII solution supports an incremental request for data between API spec 1 (405) and API spec 2 (API 407).

Figure 5:
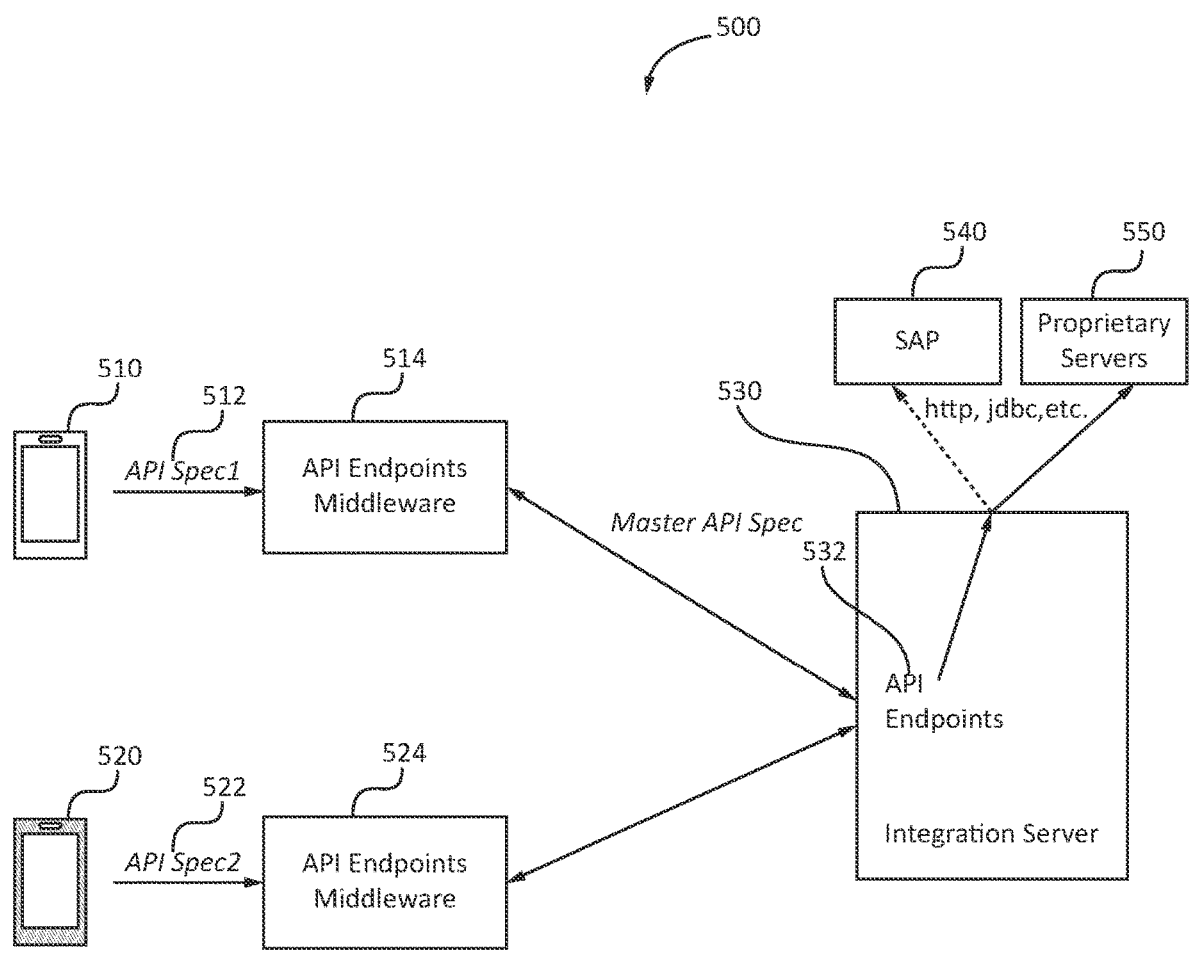
FIG. 5 is a block/flow diagram of new app development in an illustrative system.

FIG. 5 is a block/flow diagram of new app development in a system.

In a system 500, a client 510 requests an API spec 1 (512) from middleware 514. Similarly, a client 520 requests an API spec 2 (522) from middleware 524. The integration server 530 with API endpoints 532 communicates with enterprise applications such as SAP 540 and proprietary servers 550 to identify data sources, define/update the API spec, and create per client API services and updates. In such a system, large enterprise integrations, data discovery, design, and implementation takes at least three months with many months of human effort and high cost.

Figure 6:
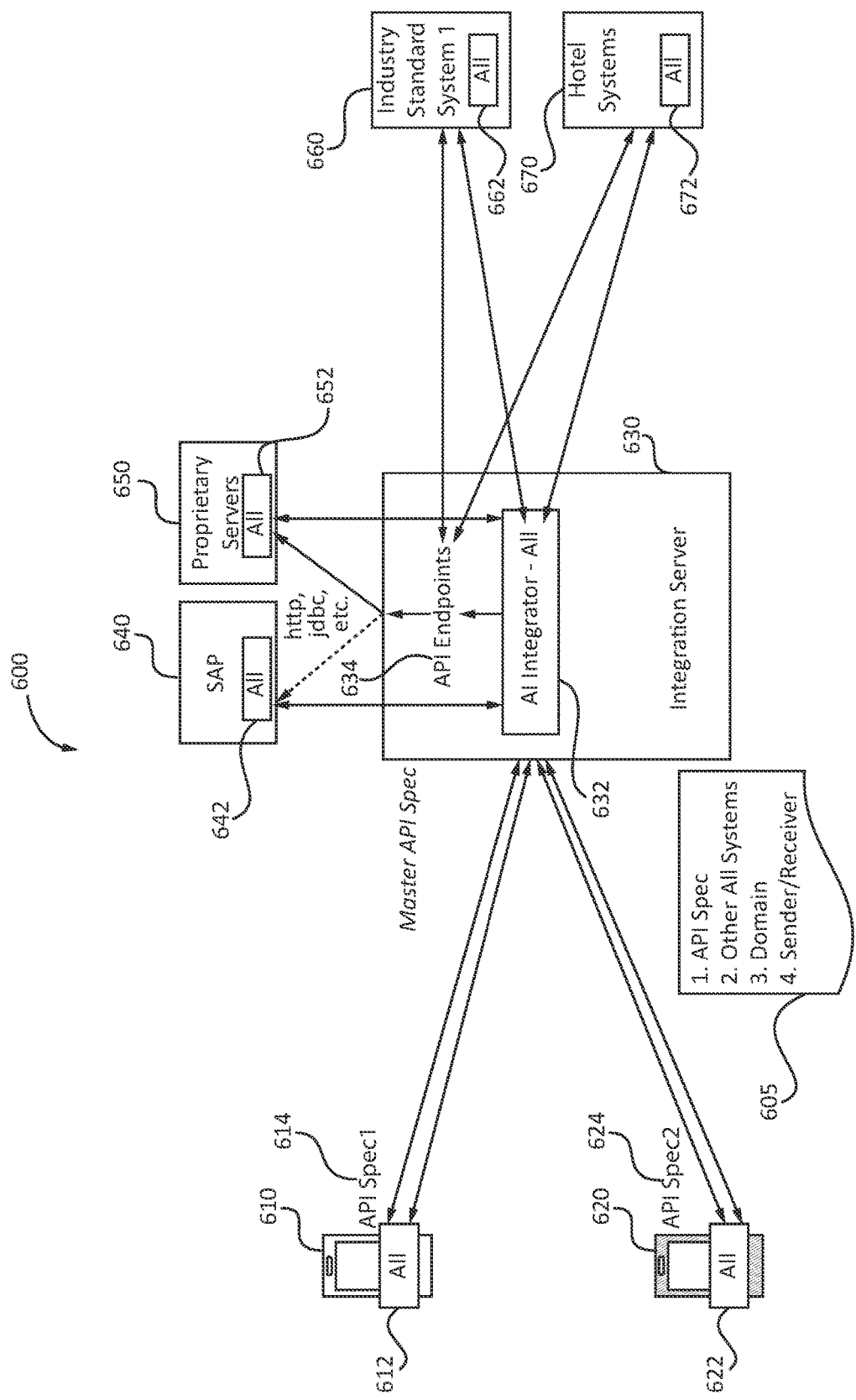
FIG. 6 is a block/flow diagram of new app development by implementing the AI integrator, in accordance with an embodiment of the present invention.

FIG. 6 is a block/flow diagram of new app development by implementing the AI integrator, in accordance with an embodiment of the present invention.

In the exemplary configuration 600, a client 610 with an AII integrator 612 requests an API spec 1 (614) and a client 620 with an AII integrator 622 requests an API spec 2 (624) from the integration server 630. The integration server 630 includes an AI integrator interface 632. The integration server 630 with API endpoints 634 communicates with enterprise applications such as SAP 640 and proprietary servers 650. The SAP 640 includes an SAP AI interface 642 and the proprietary servers 650 include a proprietary servers AI interface 652.

The AI integrator interface 632 of the integration server 630 communicates with an industry standard system 660 and a hotel system 670. The industry standard system 660 includes an industry standard AI interface 662 and the hotel system 670 and a hotel system AI interface 672.

Summary list 605 is also provided.

Therefore, in a mobile app practical application, the frontend, e.g., mobile app is provided with the user interface (UI) design. With the UI design and configuration including the domain, the AI integrator creates an API spec, as well as the service integration layer. The mobile app is built using the service integration layer provided by the AI integrator. The AI integrator in the mobile app reaches out to the AI endpoint in the backend with the API spec and establishes an AI conversation to understand the authentication mechanism and availability of services.

Stated differently, the AI integrator in the backend is trained to understand the received API spec, compare it with its own specification, data model, industry terms, and/or relationship. The AI integrator authenticates the service request and identifies if it could provide a response with its current specification and implementation. If it is a new client instance with a new API specification that the AI integrator must process, the AI integrator arrives at the alignment of API specification it received with its own API specification. The AI integrator performs the mapping from its own spec to the client provided spec. If the AII could not find the data source, the AII will look up other potential AII systems that could provide this data from its configured list. AII does an AI conversation with those systems. If there are competitive products, it can check for the best systems based on configured metrics. If the AII finds a data source, the AII completes performing the mapping and decides on deployment (e.g., with choice of configured run-time, compute needed, etc.). A workflow gets triggered or confirmation process (could be an email confirmation from server admin) to proceed. On approval, the AII generates the code and deploys for usage.

Iterative cognitive interactions enable the system to perform automatic mapping and integration of two systems which significantly reduces the time and effort involved in integration of two heterogenous systems. Using conversational AI as both requestor and consumer enables faster interpretation of different specifications and acts as a certification for any given system that it is ready for faster integration. Using artificial intelligence and machine learning for mapping ensures the accuracy and integrity of the software integration.

Figure 7:
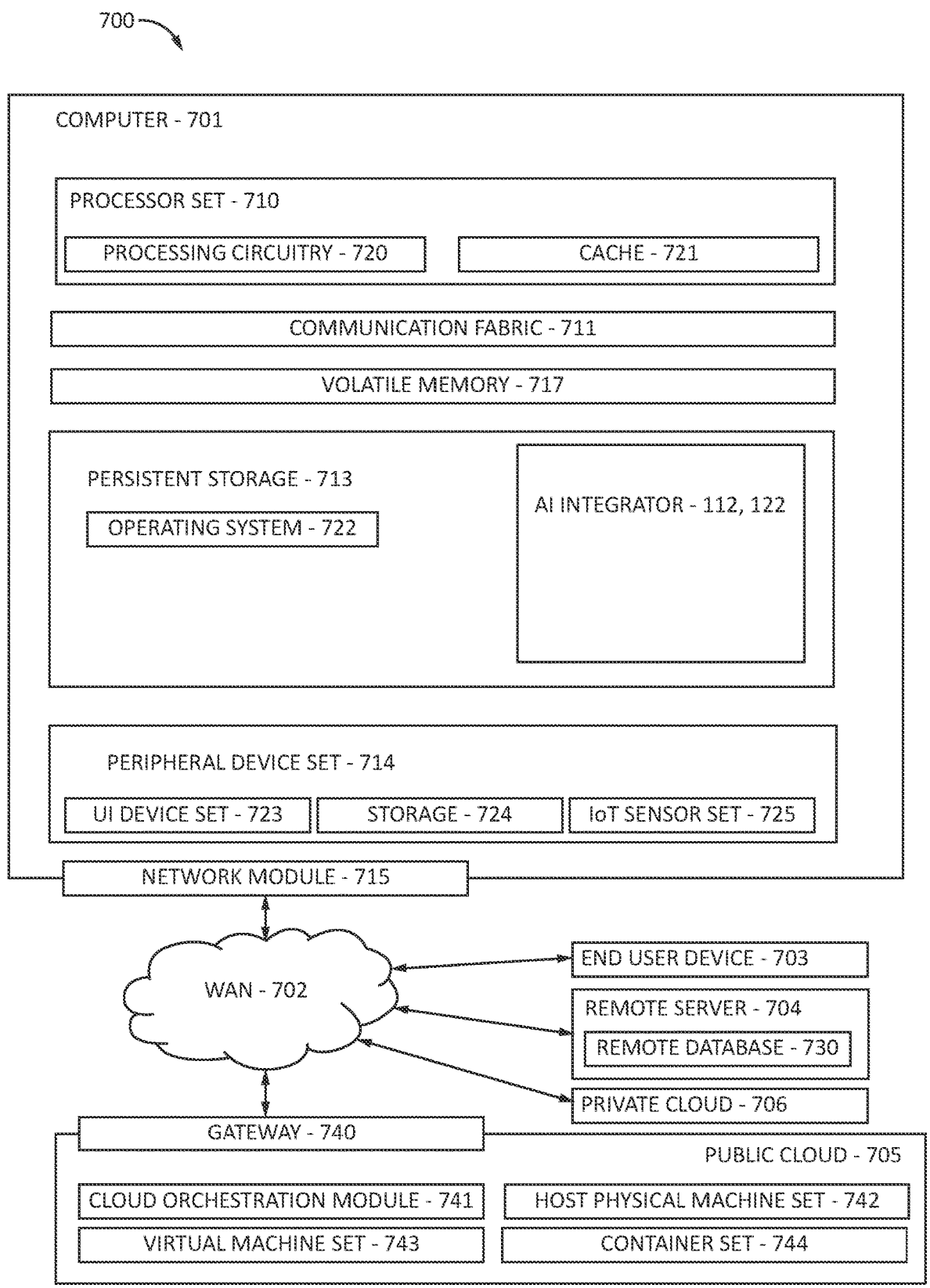
FIG. 7 is a block diagram of an exemplary computer system for applying the AI integrator, in accordance with an embodiment of the present invention.

FIG. 7 is a block diagram of an exemplary computer system for applying the AI integrator, in accordance with an embodiment of the present invention.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is usually moved at some occasional points in time during normal operations of a storage device, such as during access, de-fragmentation or garbage collection, but this does not render the storage device as transitory because the data is not transitory while it is stored.

Computing environment 700 contains an example of an environment for the execution of at least some of the computer code involved in performing the inventive methods, such as the integrator configuration or software integration system 100 with AI integrators 112, 122. In addition to block 750, computing environment 700 includes, for example, computer 701, wide area network (WAN) 702, end user device (EUD) 703, remote server 704, public cloud 705, and private cloud 706. In this embodiment, computer 701 includes processor set 710 (including processing circuitry 720 and cache 721), communication fabric 711, volatile memory 712, persistent storage 713 (including operating system 722 and block 750, as identified above), peripheral device set 714 (including user interface (UI) device set 723, storage 724, and Internet of Things (IoT) sensor set 725), and network module 715. Remote server 704 includes remote database 730. Public cloud 705 includes gateway 740, cloud orchestration module 741, host physical machine set 742, virtual machine set 743, and container set 744.

COMPUTER 701 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 730. As is well understood in the art of computer technology, and depending upon the technology, performance of a computer-implemented method may be distributed among multiple computers and/or between multiple locations. On the other hand, in this presentation of computing environment 700, detailed discussion is focused on a single computer, specifically computer 701, to keep the presentation as simple as possible. Computer 701 may be located in a cloud, even though it is not shown in a cloud in FIG. 6. On the other hand, computer 701 is not required to be in a cloud except to any extent as may be affirmatively indicated.

PROCESSOR SET 710 includes one, or more, computer processors of any type now known or to be developed in the future. Processing circuitry 720 may be distributed over multiple packages, for example, multiple, coordinated integrated circuit chips. Processing circuitry 720 may implement multiple processor threads and/or multiple processor cores. Cache 721 is memory that is located in the processor chip package(s) and is typically used for data or code that should be available for rapid access by the threads or cores running on processor set 710. Cache memories are typically organized into multiple levels depending upon relative proximity to the processing circuitry. Alternatively, some, or all, of the cache for the processor set may be located "off chip." In some computing environments, processor set 710 may be designed for working with qubits and performing quantum computing.

Computer readable program instructions are typically loaded onto computer 701 to cause a series of operational steps to be performed by processor set 710 of computer 701 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 721 and the other storage media discussed below. The program instructions, and associated data, are accessed by processor set 710 to control and direct performance of the inventive methods. In computing environment 700, at least some of the instructions for performing the inventive methods may be stored in block 750 in persistent storage 713.

COMMUNICATION FABRIC 711 is the signal conduction path that allows the various components of computer 701 to communicate with each other. Typically, this fabric is made of switches and electrically conductive paths, such as the switches and electrically conductive paths that make up buses, bridges, physical input/output ports and the like. Other types of signal communication paths may be used, such as fiber optic communication paths and/or wireless communication paths.

VOLATILE MEMORY 712 is any type of volatile memory now known or to be developed in the future. Examples include dynamic type random access memory (RAM) or static type RAM. Typically, volatile memory 712 is characterized by random access, but this is not required unless affirmatively indicated. In computer 701, the volatile memory 712 is located in a single package and is internal to computer 701, but, alternatively or additionally, the volatile memory may be distributed over multiple packages and/or located externally with respect to computer 701.

PERSISTENT STORAGE 713 is any form of non-volatile storage for computers that is now known or to be developed in the future. The non-volatility of this storage means that the stored data is maintained regardless of whether power is being supplied to computer 701 and/or directly to persistent storage 713. Persistent storage 713 may be a read only memory (ROM), but typically at least a portion of the persistent storage allows writing of data, deletion of data and re-writing of data. Some familiar forms of persistent storage include magnetic disks and solid state storage devices. Operating system 722 may take several forms, such as various known proprietary operating systems or open source Portable Operating System Interface-type operating systems that employ a kernel. The code included in block 750 typically includes at least some of the computer code involved in performing the inventive methods.

PERIPHERAL DEVICE SET 714 includes the set of peripheral devices of computer 701. Data communication connections between the peripheral devices and the other components of computer 701 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 723 may include components such as a display screen, speaker, microphone, wearable devices (such as goggles and smart watches), keyboard, mouse, printer, touchpad, game controllers, and haptic devices. Storage 724 is external storage, such as an external hard drive, or insertable storage, such as an SD card. Storage 724 may be persistent and/or volatile. In some embodiments, storage 724 may take the form of a quantum computing storage device for storing data in the form of qubits. In embodiments where computer 701 is required to have a large amount of storage (for example, where computer 701 locally stores and manages a large database) then this storage may be provided by peripheral storage devices designed for storing very large amounts of data, such as a storage area network (SAN) that is shared by multiple, geographically distributed computers. IoT sensor set 725 is made up of sensors that can be used in Internet of Things applications. For example, one sensor may be a thermometer and another sensor may be a motion detector.

NETWORK MODULE 715 is the collection of computer software, hardware, and firmware that allows computer 701 to communicate with other computers through WAN 702. Network module 715 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 715 are performed on the same physical hardware device. In other embodiments (for example, embodiments that utilize software-defined networking (SDN)), the control functions and the forwarding functions of network module 715 are performed on physically separate devices, such that the control functions manage several different network hardware devices. Computer readable program instructions for performing the inventive methods can typically be downloaded to computer 701 from an external computer or external storage device through a network adapter card or network interface included in network module 715.

WAN 702 is any wide area network (for example, the internet) capable of communicating computer data over non-local distances by any technology for communicating computer data, now known or to be developed in the future. In some embodiments, the WAN 702 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 703 is any computer system that is used and controlled by an end user (for example, a customer of an enterprise that operates computer 701), and may take any of the forms discussed above in connection with computer 701. EUD 703 typically receives helpful and useful data from the operations of computer 701. For example, in a hypothetical case where computer 701 is designed to provide a recommendation to an end user, this recommendation would typically be communicated from network module 715 of computer 701 through WAN 702 to EUD 703. In this way, EUD 703 can display, or otherwise present, the recommendation to an end user. In some embodiments, EUD 703 may be a client device, such as thin client, heavy client, mainframe computer, desktop computer and so on.

REMOTE SERVER 704 is any computer system that serves at least some data and/or functionality to computer 701. Remote server 704 may be controlled and used by the same entity that operates computer 701. Remote server 704 represents the machine(s) that collect and store helpful and useful data for use by other computers, such as computer 701. For example, in a hypothetical case where computer 701 is designed and programmed to provide a recommendation based on historical data, then this historical data may be provided to computer 701 from remote database 730 of remote server 704.

PUBLIC CLOUD 705 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 705 is performed by the computer hardware and/or software of cloud orchestration module 741. The computing resources provided by public cloud 705 are typically implemented by virtual computing environments that run on various computers making up the computers of host physical machine set 742, which is the universe of physical computers in and/or available to public cloud 705. The virtual computing environments (VCEs) typically take the form of virtual machines from virtual machine set 743 and/or containers from container set 744. It is understood that these VCEs may be stored as images and may be transferred among and between the various physical machine hosts, either as images or after instantiation of the VCE. Cloud orchestration module 741 manages the transfer and storage of images, deploys new instantiations of VCEs and manages active instantiations of VCE deployments. Gateway 740 is the collection of computer software, hardware, and firmware that allows public cloud 705 to communicate through WAN 702.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 706 is similar to public cloud 705, except that the computing resources are only available for use by a single enterprise. While private cloud 706 is depicted as being in communication with WAN 702, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 705 and private cloud 706 are both part of a larger hybrid cloud.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), FPGAs, and/or PLAs.

These and other variations of a hardware processor subsystem are also contemplated in accordance with embodiments of the present invention.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It is also noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Having described preferred embodiments for integrating heterogeneous systems (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A method for integrating heterogeneous systems, the method comprising:
   initiating a conversation between a consumer system having a first artificial intelligence (AI) integrator and a producer system having a second AI integrator;
   training the first and second AI integrators to enable the conversation between the consumer system and the producer system;
   upon a data request from a client, enabling the consumer system to receive an application programming interface specification (API Spec) and locate the producer system that provides service in conformance with the API Spec;
   determining missing data needed to conform to the API Spec to build source code;
   if the producer system determines that it can support the data request, triggering the producer system to generate a contract; and
   after consensus is provided, in a deployment phase, generating by the producer system the source code to provide information pertaining to the data request.

2. The method of claim 1, wherein the training enables the consumer system to understand its role, understand input and output needs, understand format, business context, and perform mapping between system context summary with the input and output.

3. The method of claim 1, wherein the training allows the first AI integrator to understand specifications of different software programs in an integration context.

4. The method of claim 1, wherein the contract includes a sample response that satisfies the API Spec, an authentication mechanism, a data format, and pricing information.

5. The method of claim 4, wherein, in an evaluation phase, the consumer system evaluates the sample response, interprets the authentication mechanism, and if in an agreement, provides the consensus.

6. The method of claim 5, wherein the evaluation phase includes evaluation of data sufficiency, data format compatibility, and pricing assessment.

7. The method of claim 1, wherein, if the producer system determines that data is missing and deviations are identified, the producer system reaches out to other configured AI integrators to obtain the missing data.

8. A computer program product comprising a computer readable storage medium having program instructions embodied therewith for integrating heterogeneous systems, the program instructions executable by a computer to cause the computer to:
- initiate a conversation between a consumer system having a first artificial intelligence (AI) integrator and a producer system having a second AI integrator;
- train the first and second AI integrators to enable the conversation between the consumer system and the producer system;
- upon a data request from a client, enable the consumer system to receive an application programming interface specification (API Spec) and locate the producer system that provides service in conformance with the API Spec;
- determine missing data needed to conform to the API Spec to build source code;
- if the producer system determines that it can support the data request, trigger the producer system to generate a contract; and
- after consensus is provided, in a deployment phase, generate by the producer system the source code to provide information pertaining to the data request.

9. The computer program product of claim 8, wherein the training enables the consumer system to understand its role, understand input and output needs, understand format, business context, and perform mapping between system context summary with the input and output.

10. The computer program product of claim 8, wherein the training allows the first AI integrator to understand specifications of different software programs in an integration context.

11. The computer program product of claim 8, wherein the contract includes a sample response that satisfies the API Spec, an authentication mechanism, a data format, and pricing information.

12. The computer program product of claim 11, wherein, in an evaluation phase, the consumer system evaluates the sample response, interprets the authentication mechanism, and if in an agreement, provides the consensus.

13. The computer program product of claim 12, wherein the evaluation phase includes evaluation of data sufficiency, data format compatibility, and pricing assessment.

14. The computer program product of claim 8, wherein, if the producer system determines that data is missing and deviations are identified, the producer system reaches out to other configured AI integrators to obtain the missing data.

15. A system for integrating heterogeneous systems, the system comprising:
- a memory; and
- one or more processors in communication with the memory configured to:
  - initiate a conversation between a consumer system having a first artificial intelligence (AI) integrator and a producer system having a second AI integrator;
  - train the first and second AI integrators to enable the conversation between the consumer system and the producer system;
  - upon a data request from a client, enable the consumer system to receive an application programming interface specification (API Spec) and locate the producer system that provides service in conformance with the API Spec;
  - determine missing data needed to conform to the API Spec to build source code;
  - if the producer system determines that it can support the data request, trigger the producer system to generate a contract; and
  - after consensus is provided, in a deployment phase, generate by the producer system the source code to provide information pertaining to the data request.

16. The system of claim 15, wherein the training enables the consumer system to understand its role, understand input and output needs, understand format, business context, and perform mapping between system context summary with the input and output.

17. The system of claim 15, wherein the training allows the first AI integrator to understand specifications of different software programs in an integration context.

18. The system of claim 15, wherein the contract includes a sample response that satisfies the API Spec, an authentication mechanism, a data format, and pricing information.

19. The system of claim 18, wherein, in an evaluation phase, the consumer system evaluates the sample response, interprets the authentication mechanism, and if in an agreement, provides the consensus.

20. The system of claim 19, wherein the evaluation phase includes evaluation of data sufficiency, data format compatibility, and pricing assessment.

* * * * *